(12) United States Patent
Bryan et al.

(10) Patent No.: US 10,295,493 B2
(45) Date of Patent: May 21, 2019

(54) SAMPLING PLATE WITH VARIABLE HEIGHT TESTING ZONES

(71) Applicants: Brytech Design & Engineering Project Management Limited, Amblecote, West Midlands (GB); Tape Specialities Limited, Pitstone, Bedfordshire (GB)

(72) Inventors: Matthew Bryan, Baildon (GB); Stuart Seagrave, Pitstone (GB)

(73) Assignees: BRYTECH DESIGN & ENGINEERING PROJECT MANAGEMENT LIMITED, Amblecote, West (GB); TAPE SPECIALITIES LIMITED, Pitstone, Bedfordshire (GB)

( * ) Notice: Subject to any disclaimer, the term of this patent is extended or adjusted under 35 U.S.C. 154(b) by 0 days.

(21) Appl. No.: 15/034,764

(22) PCT Filed: Nov. 7, 2014

(86) PCT No.: PCT/GB2014/053323
§ 371 (c)(1),
(2) Date: May 5, 2016

(87) PCT Pub. No.: WO2015/067960
PCT Pub. Date: May 14, 2015

(65) Prior Publication Data
US 2016/0290949 A1    Oct. 6, 2016

(30) Foreign Application Priority Data
Nov. 7, 2013   (GB) .................................. 1319703.3

(51) Int. Cl.
*B01L 3/00*      (2006.01)
*G01N 27/327*    (2006.01)
*C12Q 1/00*      (2006.01)

(52) U.S. Cl.
CPC ......... *G01N 27/3272* (2013.01); *C12Q 1/006* (2013.01)

(58) Field of Classification Search
CPC ............. B01L 3/5027; B01L 3/502707; B01L 3/502753; B01L 2300/0887; B01L 2300/0893
(Continued)

(56) References Cited

U.S. PATENT DOCUMENTS

2005/0249633 A1   11/2005   Blatt et al.
2007/0161102 A1    7/2007   Yang et al.
2007/0280857 A1   12/2007   Song et al.

FOREIGN PATENT DOCUMENTS

GB   2501128    10/2013
WO   0042430     7/2000
(Continued)

OTHER PUBLICATIONS

International Search Report and written Opinion of the ISA for application No. PCT/GB2014/053323 dated Feb. 3, 2016 10 pages.
(Continued)

*Primary Examiner* — Jill A Warden
*Assistant Examiner* — Dwayne K Handy
(74) *Attorney, Agent, or Firm* — Niels Haun; Dann, Dorfman, Herrell & Skillman, P.C.

(57) ABSTRACT

A sampling plate (1) for use in measuring a property of a fluid sample comprising a sample zone comprising at least two discrete testing zones (5, 6) for receiving different respective volumes of the fluid sample. Each testing zone presents a zone volume defined by a respective zone area
(Continued)

and a different respective zone height being a dimension transverse to the zone area (A).

16 Claims, 8 Drawing Sheets

(58) Field of Classification Search
USPC .................................................. 422/502, 503
See application file for complete search history.

(56) References Cited

FOREIGN PATENT DOCUMENTS

| WO | 2006/015615 | 2/2006 |
|---|---|---|
| WO | 2007/025559 | 3/2007 |
| WO | 2010/038050 | 4/2010 |
| WO | 2011121352 | 10/2011 |
| WO | 2011124906 | 10/2011 |

OTHER PUBLICATIONS

GB Search Report for GB application No. 1319703.3 dated May 5, 2015 4 pages.
Office action in corresponding European application 14799848.8; dated Jul. 25, 2017.

SAMPLING PLATE WITH VARIABLE HEIGHT TESTING ZONES

PRIORITY APPLICATIONS

This application is a 371 application of International Application No. PCT/GB2014/053323 filed Nov. 7, 2014, which claims priority to United Kingdom Patent Application No. 1319703.3 filed Nov. 7, 2013. Each of the foregoing applications is hereby incorporated herein by reference.

INTRODUCTION

The present invention relates to a sampling plate. In particular the invention relates to a sampling plate for measuring certain selected properties of a liquid sample, such as the glucose levels in a blood sample. The invention also relates to the control of fluid samples once they are applied to the sampling plate, e.g. for diagnostic testing.

INTRODUCTION TO THE BACKGROUND ART

There is a widespread need for sampling plates such as those which, when used in conjunction with a measurement device, enable a diabetes patient to know their blood sugar levels—i.e. the concentration of glucose in their blood.

Traditional sampling plates function by receiving a spotted blood sample and directing at least some of the blood to a testing zone. The testing zone typically takes the form of a recess or well containing a quantity of glucose oxidase which chemically reacts with the blood to an extent and at a rate determined by the glucose concentration in the blood. The testing zone is typically furnished with a pair of electrode terminals which are conveniently bridged by the reaction mixture of the blood and glucose oxidase so as to allow for electrochemical readings by a corresponding measurement device. The electrochemical readings then provide an indication of blood glucose levels.

A problem with some such traditional sampling plates is that a single testing zone permits only the application of a single diagnostic test to the sample. Some traditional sampling plates have multiple testing zones formed in the plate to allow multiple diagnostic tests to be performed on a sample. However, blood spreading in and to the testing zone is often slow. For instance, blood spreading is often inhibited by air present in a testing zone which must be displaced by an initial blood flow. Sometimes a blood sample will not spread throughout the testing zone, and consequently measurements may be inaccurate or unreliable. This is a particular problem for sampling plates having larger testing zones.

It is an object of the present invention to provide an improved sampling plate.

SUMMARY OF THE INVENTION

The invention, at its most general, has followed a realisation that detecting the presence of an analyte in a fluid sample or measuring the concentration of analyte in a fluid sample depends not only upon the detection/measurement technique employed but also the fluid sample size used. Certain analytes may preferably be detected/measured according to a selected one of several different techniques which may each require relatively larger or smaller sample sizes in order to be most, or more, effective.

It has been realised that if one requires to detect/measure the concentration of a plurality of analytes in a fluid sample using the same sampling plate it may be beneficial to divide the fluid sample into areas that have different respective specific volumes chosen according to the preferences of the detection/measurement technique intended to be applied to the sample within that specific volume.

According to the invention, by providing a sampling plate having testing zones with a floor on which the fluid sample may flow (e.g. the X-Y plane of the testing zone), a transverse dimension of the testing zone (e.g. the Z dimension, orthogonal to the X-Y plane) may be different for different testing zones thereby to control the volumes of the testing zones at least in the transverse dimension.

Traditional sampling plates may be able to direct fluidic samples in a number of pathways to serve a number of sensor areas located on the X-Y plane of the plate. However the fluid sample remains at a constant thickness (e.g. the Z dimension) throughout the plate.

The invention disclosed in preferred embodiments herein includes an apparatus for implementing control of a fluid sample in the X, Y and Z directions to serve a plurality of separate testing zones some or all of which may be arranged to apply different respective detection/measurement techniques to a fluid sample.

According to a first aspect of the present invention there is provided a sampling plate, comprising a sample zone comprising at least two discrete/separate testing zones for receiving different respective volumes of the fluid sample. Each testing zone presents a zone volume defined by a respective zone area and a different respective zone height being a dimension transverse to the zone area. The testing zones may be discrete or separate in the sense that their separation forms "discrete" zones/volumes which are fully separated from each other. The discrete/separated zones may be in fluid communication via one or more channels, paths or conduits. This separation permits separate respective sample volumes to be formed within the separate zones.

Herein, a "sampling plate" may mean any surface capable of receiving a liquid sample in a sample zone. Preferably, however, the sampling plate is portable. Suitably the sampling plate may cover an area less than 1 m², preferably less than 50 cm², more preferably less than 10 cm² and most preferably less than 5 cm². The sampling plate may cover an area less than 500 mm²—for instance 350 mm² where the sampling plate is 10 mm wide by 35 mm long. Suitably the sampling plate may be rectangular. The sampling plate may be a strip, and may be a flexible strip. Preferably, however, the sampling plate is an individual plate, preferably a rigid sampling plate. The thickness of the sampling plate is preferably less than 1 cm, preferably less than 1 mm, more preferably less than 0.5 mm, most preferably less than 0.25 mm.

The size of a respective zone area may be common to some or all of the testing zones.

The sampling plate may include a sample loading port in fluid communication with the plurality of testing zones. "In fluid communication with" may mean interfacing, where "interfacing" means sharing a common boundary.

Some or all of the zone areas may be substantially coplanar.

A zone volume may be substantially defined by the product of the respective said zone area and zone height.

The sampling plate may comprise an air porous body which is in fluid communication with one, some or each of the testing zones wherein the air porous body is arranged to receive air displaced from the testing zones as the liquid sample is received into the testing zone. Preferably "in fluid communication with" refers to where the air porous body is adjacent to the testing zone. The air porous body may define a wall(s) of the testing zone. The air porous body may surround the testing zone. Preferably the air porous body defines the testing zone, or defines an outer boundary of the testing zone. Preferably the air porous body defines the perimeter of the testing zone or at least part of the perimeter of the testing zone. Preferably the air porous body is external to the testing zone itself. Preferably the testing zone is free of air porous body. Preferably the air porous body is arranged to receive displaced air as the liquid sample approaches the air porous body. Preferably the air porous body is arranged to receive air displaced in the same direction as the liquid sample travels (or spreads) into the testing zone. Preferably the air porous body is arranged to receive a side-ways displacement of air as the liquid sample approaches the air porous body in a side-ways manner.

An advantage of the present invention is that the air porous body helps the liquid sample to flow into the testing zone with minimal air resistance, by providing a means by which air can be directly displaced—preferably in the same direction as the liquid sample enters the testing zone. This permits the liquid sample to enter the testing zone at a faster rate. In contrast, where such an air porous body is absent, air resistance retards the flow of the liquid sample into the testing zone.

Another advantage of the present invention is that the air porous body helps the liquid sample to spread uniformly throughout the testing zone, thus giving greater sampling consistency and consequently more accurate measurements. In contrast, where the air porous body is absent, air resistance affects the fluid dynamics of the liquid sample by discouraging spreading (air resistance from all sides) and instead encouraging the liquid sample to remain collectively associated as a bulk (aided by surface tension). As such the liquid sample tends to flow as a bulk in a single direction since in this way the bulk overcomes air resistance in that particular direction.

Another advantage is that formation of air-pockets is alleviated, which again allows for better spreading and more accurate measurements.

The air porous body is preferably substantially impermeable to the liquid sample. The air porous body is preferably substantially impermeable to water. The air porous body is preferably substantially impermeable to an aqueous liquid sample, and most preferably substantially impermeable to blood.

The air porous body is preferably impermeable to water (at standard temperature and pressure) to the extent that the air porous body remains visibly wet for at least 15 seconds, preferably at least 30 seconds, more preferably at least 1 minute, most preferably at least 10 minutes, after wetting a portion of the air porous body with the smallest drop of water required to impart visible wetness.

The air porous body is preferably suitable for containing 100% of the liquid sample for at least 15 seconds, more preferably for at least 1 minute, and most preferably at least 10 minutes. The air porous body is preferably totally impermeable to the liquid sample, water, an aqueous liquid sample, or a blood sample. Such impermeability is preferably imparted by the hydrophobicity of the air porous body rather than the small size of its pores. Most preferably the air porous body is arranged to contain the liquid sample in the sample zone. Preferably the air porous body is arranged to hold the liquid sample, preferably an aqueous liquid sample, and more preferably blood, within the testing zone.

Preferably the perimeter of the testing zone comprises a wall. Preferably the perimeter (or wall) of the testing comprises at least some air porous body. In some embodiments at least 50% of the perimeter may comprise air porous body. The air porous body is preferably located substantially around the perimeter of the testing zone. Preferably a floor of the testing zone is free of air porous body. Where the testing zone comprises a roof, the roof is preferably free of air porous body.

The air porous body preferably comprises hydrophobic material. Preferably the air porous body comprises at least 50 wt %, more preferably at least 70 wt %, and most preferably at least 90 wt % hydrophobic material. In some embodiments the air porous body may comprise a mixture of hydrophobic and hydrophilic material. Preferably the air porous body is hydrophobic overall (i.e. has a net hydrophobicity). Hydrophobicity may be measured by considering techniques well known in the art. In general, the air porous body exhibits the requisite net hydrophobicity where a drop of water rolls off the surface of the air porous body when such a surface is inclined at least 30° from horizontal, preferably at least 20° from horizontal, and most preferably at least 10° from horizontal.

The porosity of a porous material generally describes a fraction of void space (capable of containing fluids) in the porous material, and may be expressed as:

$$\phi = V_v / V_T;$$

where $V_v$ is the volume of void space, and $V_T$ is the total volume of material including void space. There are a number of ways of measuring porosity, including:

Direct methods—determining the bulk volume of the porous material and then determining the volume of skeletal material with no pores (pore volume=total volume—skeletal material volume);

Optical methods—determining the area of the material versus the area of the pores visible under a microscope. This method is accurate for materials with random structure since areal porosity and volumetric porosity is then the same.

Imbibition methods—immersing the porous material, under vacuum, in a fluid the preferentially wets the pores. In this case a non-hydrophilic fluid would be preferred which does not dissolve the air porous body. Those skilled in the art would readily select a suitable solvent. (pore volume=total volume of fluid−volume of fluid left after soaking).

Fluid evaporation method (pore volume is a function of: weight of a porous material saturated with fluid−weight of dried air porous body).

Many other methods are also known in the art.

The air porous body preferably has a porosity of at least 0.001, preferably at least 0.01, more preferably at least 0.1, and most preferably at least 0.2. The air porous body preferably has a porosity of at most 0.95, preferably at most 0.90, more preferably at most 0.8, and most preferably at most 0.7. The most preferably porosity is between 0.3 and 0.4. A porosity lower than the preferred minimum impedes air displacement. A porosity above the preferred maximum risks the air porous body becoming moderately permeable to the liquid sample, particularly water or blood.

The air porous body preferably has an average pore size between 10 and 300 microns, preferably between 50 and 200 microns, and most preferably between 100 and 150 microns. Pores of the air porous body are preferably free from blockage by a pore blocking substance. For instance, the pore blocking substance may include an adhesive, especially an adhesive for adhering the air porous body to the sampling plate. The air porous body is must preferably, of course, porous when incorporated into the sampling plate. The extent of pore blocking is the extent to which the void space of the air porous body (i.e. the space of the pores) is occupied by the pore blocking material, as measurable in accordance with the above techniques or others well known in the art. Preferably the pores of the air porous body are less than 70% blocked, preferably less than 50% blocked, more preferably less than 30% blocked, and most preferably less than 10% blocked.

The air porous body preferably has a porosity of 0.2 or more. The air porous body may comprise a mesh. The mesh may comprise polyether ether ketone (PEEK), polypropylene (PP), polyester (PET), polyvinylidene fluoride (PVDF), ethylene chlorotrifluoroethylene (ECTFE), ethylene co-tetrafluoroethylene (ETFE), nylon (polyamide), or fluorinated ethylene-propylene (FEP).

The air porous body may be a porous layer of the sampling plate, the layer comprising an empty portion arranged to receive and contain the liquid sample within a respective testing zone.

The air porous body is preferably located substantially around the perimeter of a respective testing zone.

The sampling plate may comprise a plurality of separate air-porous bodies mutually spaced by a spacer body in the dimension transverse to the zone areas.

A, some or each, spacer body may be a non-porous layer of the sampling plate, the layer forming a said zone area in one or more said testing zones and forming an empty portion arranged to receive and contain the liquid sample within one or more other said testing zones. One, some or each spacer body may present a hydrophilic surface to a respective testing zone of which it forms a part. In particular surface of one or each of the spacer bodies which defines a floor or ceiling of a testing zone may be hydrophilic. The spacer body may comprise a hydrophilic material which may be a coating upon the spacer body, or may be substantially the material forming the spacer body. The hydrophilic surface may preferably be such as to produce a wetting angle of less than 30 degrees. The sampling plate may comprise transparent layers at the floor and ceiling of one, some or each of the testing zone(s) to allow light paths to pass through them and through any samples within testing zones. This permits photometric testing of samples. The sampling plate may comprise conductive electrodes formed on the floor or ceiling of one, some or each of the testing zone(s) to allow electrical signals to pass between them when, in use, bridged by a liquid sample therein.

The plurality of air-porous bodies may share a substantially common thickness in the transverse dimension.

The sampling plate may comprise a plurality of spacer bodies which share a substantially common thickness in the transverse dimension.

The air porous body is preferably substantially impermeable to water. The air porous body is preferably arranged to hold the liquid sample within the sample zone. The air porous body preferably comprises hydrophobic material.

Each testing zone is preferably accessible via a zone loading port for loading fluid sample into the testing zone, and having substantially the same height as the height of the associated testing zone.

The sample zone preferably comprises at least one hydrophilic floor for containing the liquid sample.

In a second aspect, the invention may provide a method of manufacturing a sampling plate for use in measuring a property of a fluid sample, comprising providing a plurality of separate air-porous layers each comprising an empty portion arranged to receive and contain the fluid sample, providing one or more spacer layers each comprising an empty portion arranged to receive and contain the liquid sample, forming a laminate of layers comprising a plurality of the air-porous layers each mutually spaced by a spacer to form a sampling plate layer in which respective the empty portions are in register to define at least two discrete testing zones for receiving different respective volumes of the fluid sample. Each testing zone presents a zone volume defined by a respective zone area and a different respective zone height defined by the laminate of layers in a dimension transverse to the zone area.

BRIEF DESCRIPTION OF THE DRAWINGS

In the drawings, like items are assigned like reference symbols.

DETAILED DESCRIPTION

Figure 1:
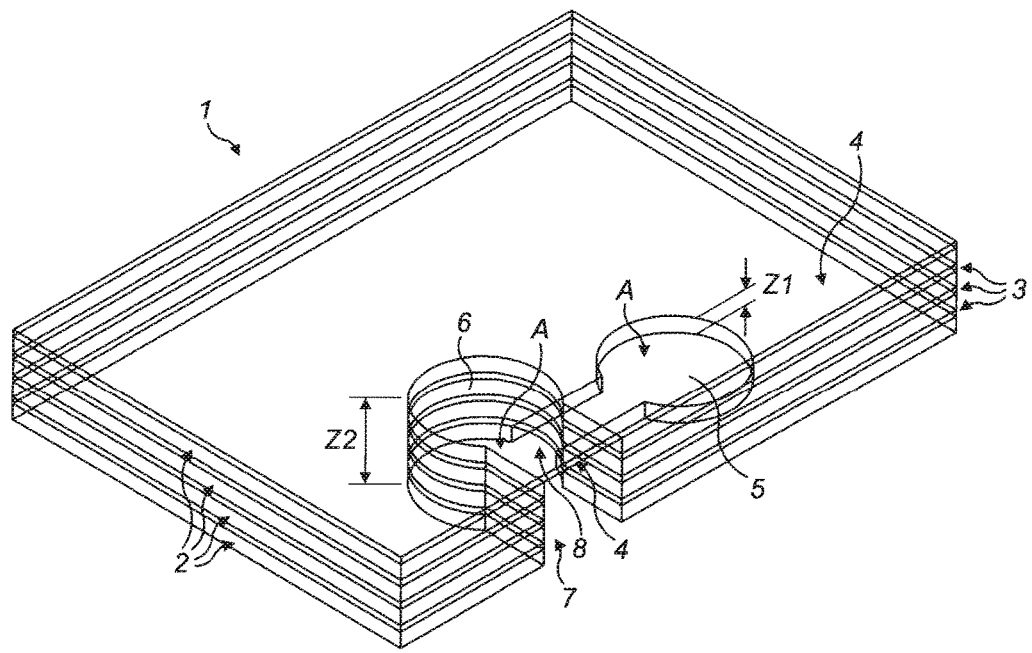
FIG. 1 illustrates a transparent view of a sample zone laminate structure having two discrete testing zones, for a sampling plate according to an embodiment of the invention.
Figure 2A:
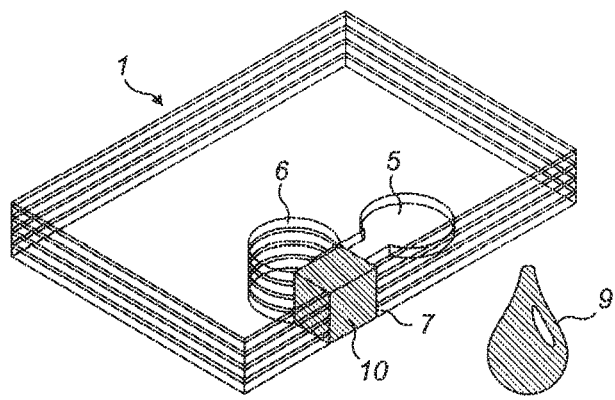
FIGS. 2A, 2B and 2C collectively illustrate successive stages in the loading of a liquid blood sample into the two discrete testing zones of the sample zone laminate structure of FIG. 1.
Figure 2B:
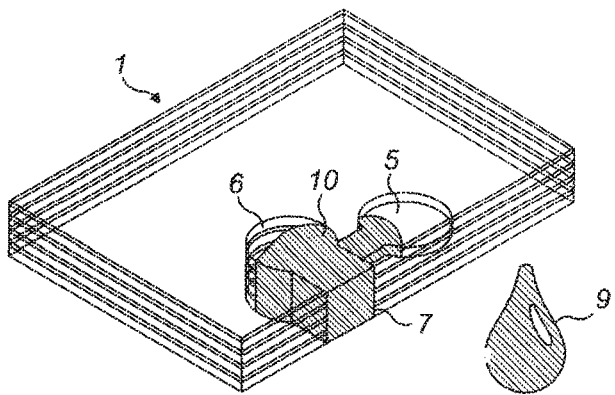
Figure 2C:
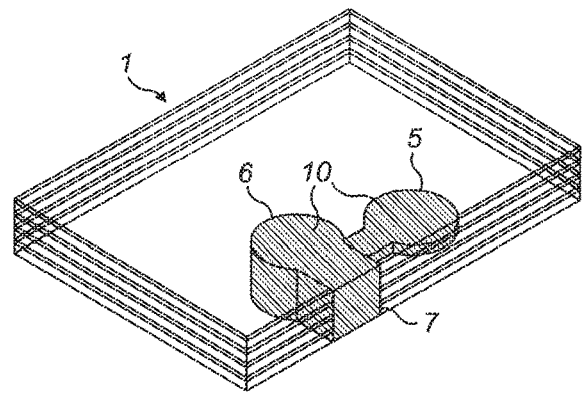
Figure 3:
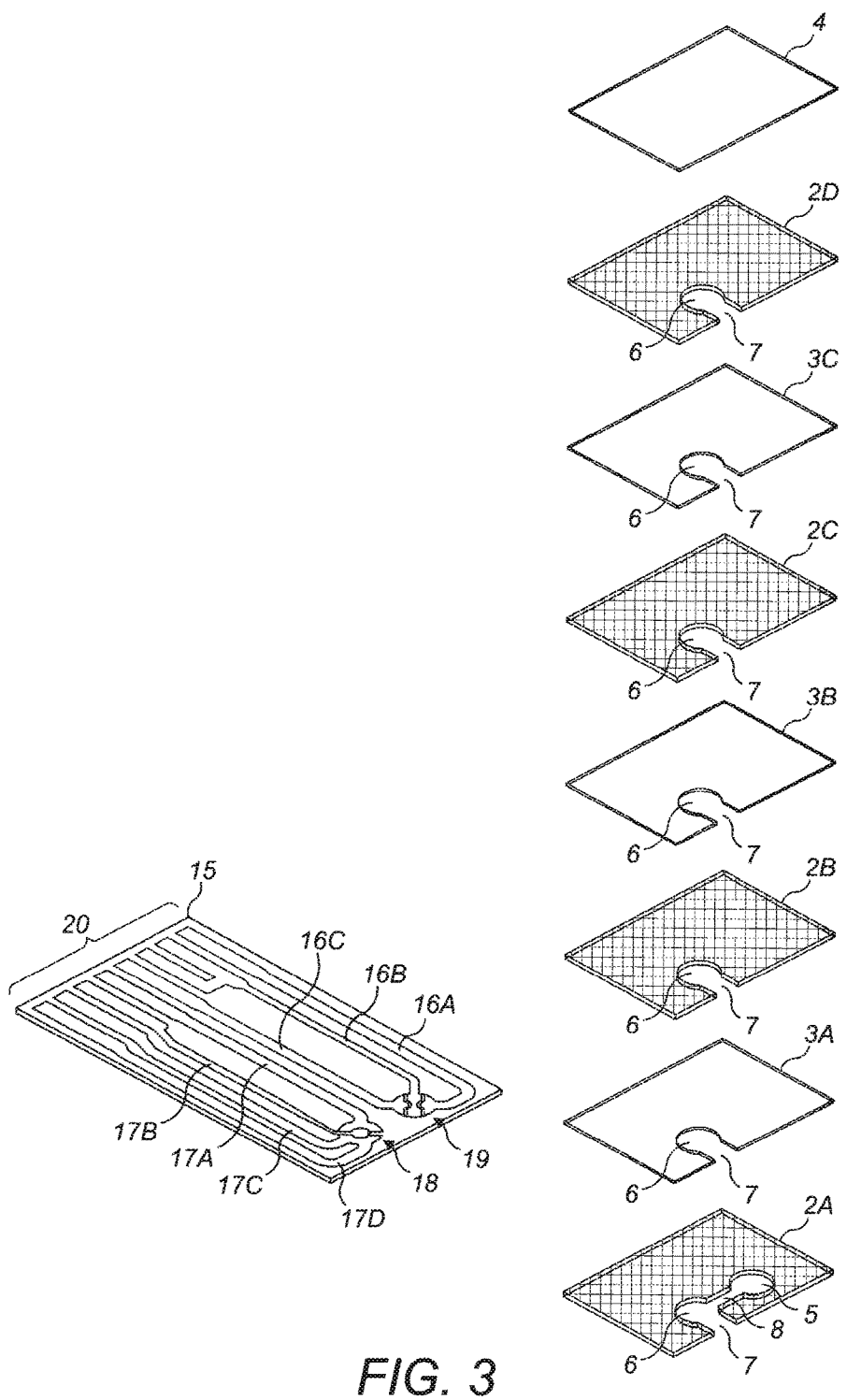
FIG. 3 illustrates an exploded view of the components of a sampling plate comprising the sample zone laminate structure of FIGS. 1 to 2C.
Figure 4A:
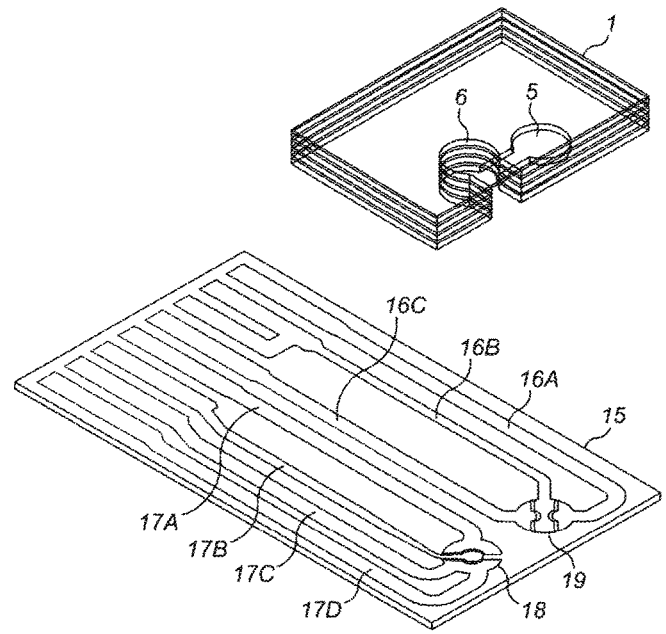
FIGS. 4A and 4B illustrate views of a sampling plate of FIG. 3. An exploded view is shown in FIG. 4A, and a view of the assembled sampling plate is shown in FIG. 4B.
Figure 4B:
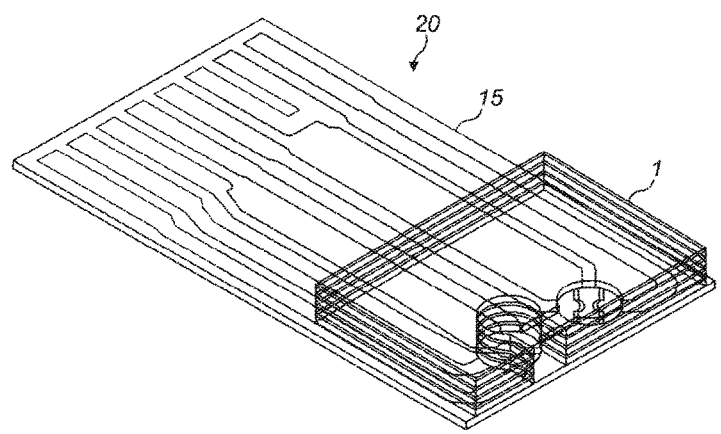

FIG. 1 illustrates (in isolation for clarity) a sample zone laminate structure 1 forming a part of the sampling plate 20 shown in FIGS. 3, 4A and 4B. These figures are to be viewed in conjunction in the following description. The sampling plate comprises the sampling zone laminate structure affixed to a surface of a support plate 15 bearing electrodes which will be described in detail below. The support plate is omitted from FIGS. 1 and 2A to 2C for clarity only.

The sample zone comprises two discrete testing zones (5, 6), each for receiving different respective volumes of a fluid blood sample. Each testing zone presents a zone volume defined by the product of a respective zone base area ("A"; diameter e.g. 1.6 mm) and a different respective zone height ("Z1"=250 microns, "Z2"=4×Z1=1 mm) being a dimension transverse to the zone area.

FIGS. 2A, 2B and 2C schematically illustrate the manner in which a volume 10 of a liquid blood sample 9 may enter and completely fill the two testing zones (5, 6) via a sample loading port 7 in fluid communication with each testing zone. To load and fill the testing zones, the fluid blood sample 9 is placed initially in fluid communication with the sample loading port 7 and is drawn into the loading port by capillary action. Further capillary action draws the fluid 10 into the first of the two testing zones 6 and then into the second of the two testing zones 5 via a fluid communication channel 8 linking the two testing zones. Air displaced from the volume of the two testing zones, and from the loading port and fluid communication channel, is received into air-porous laminar parts of the body of the sample zone by the advancing mass of liquid blood sample. This means that air bubbles which cause blockages to sample flow into the testing zones, can be avoided or greatly minimised.

The end result, shown in FIG. 2C, is a fully loaded sample zone comprising two separate blood samples 10 of different, known respective volumes (controlled by the geometry of the testing zones) in respective testing zones (5, 6), ready for testing. The air-porosity of the sample zone permits accurate, repeatable and reliable flow of liquid samples into the testing zones thereby enabling the sample to fill each testing zone fully and to allow the user be confident that the volume of sample in a given testing zone substantially corresponds to the volume of the testing zone itself. As a result, different test may be confidently applied to the different volumes of sample according to the size of the volume as appropriate/desired. It is also noted that the efficiency of fluid sample flow to fill the testing zones permits the use of a single sample loading port 7 to serve all of the testing zones of the sample zone. The provision of one sample loading port in this way makes the loading of the fluid sample easier and quicker than would be the case if two or more sample loading ports were employed. However, in alternative embodiments, additional, separate sample loading ports may be employed in fluid communication with one or more resting zones of the sample zone, if desired.

Fluid communication channel 8 stems off from one side of the first testing zone 6 substantially in a perpendicular direction to the direction of the loading port 7. This may be an advantage in that both of the testing zones (5, 6) are permitted to fill with liquid sample at about the same time which may be desirable depending upon the diagnostic testing being performed upon the sample. For example, one of the testing zones may contain a reactive agent (e.g. an enzyme) whereas the other may not. In such circumstances it may be desirable to perform concurrent measurements upon both samples in both testing zones quickly, and undesirable to have a delay between the filling one testing zone and the next—e.g. as may occur if the communication channel 8 were positioned as a linear, parallel continuation of the loading port 7 extending from the far end of the first testing zone. Of course, this latter, linear geometry may be desirable in other tests and for other reasons.

Figure 5:
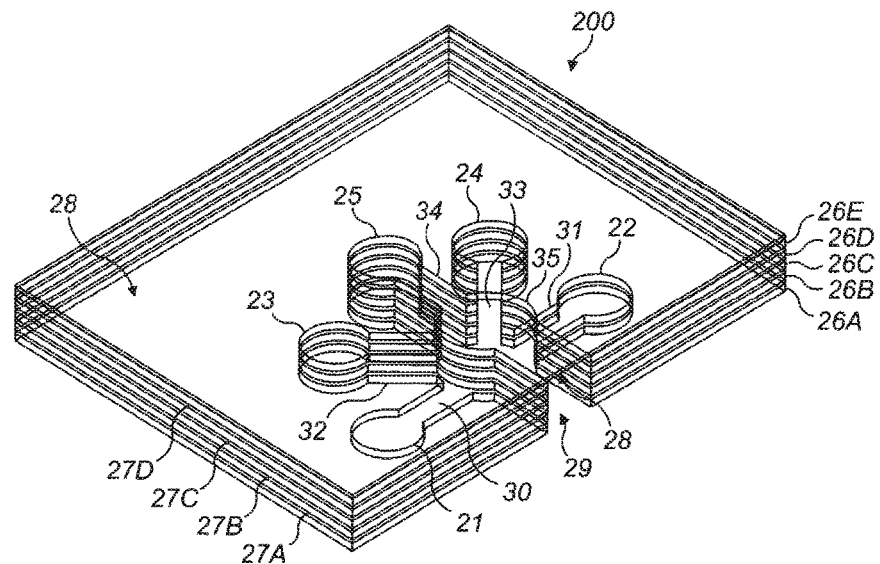
FIG. 5 illustrates a transparent view of a sample zone laminate structure having five discrete testing zones, for a sampling plate according to an embodiment of the invention.

Furthermore, it is noted that the height of the loading port matches the height of the highest testing zone (zone 6 of FIG. 1; zone 25 of FIG. 5). This geometry assists in greatly in allowing capillary action to draw sample liquid into the testing zones through the loading port.

The support plate 15 comprises a plane rectangular base plate formed from a non-conductive and resiliently flexible material, such as a plastics material. Formed upon a common flat surface of the base plate are a plurality of separate, conductive electrical signal conduction tracks (16A, 16B, 16C, 17A, 17B, 17C and 17D). The tracks may be thin printed layers of Gold or other suitable electrical signal conduction material such as printed carbon and/or silver.

A first group of four of these conductive tracks (17A, 17B, 17C and 17D) extend in parallel from a signal input/output end of the support plate and converge to form a first mutual, terminal electrode formation 18 in which terminal ends of the conductive tracks of the first group are shaped and arranged in a predetermined pattern and geometry dictated by the particular electro-chemical testing procedure they are intended to support for testing a blood sample of a selected/appropriate first sample volume. A second group of three of the conductive tracks (16A, 16B, 16C) also extend in parallel from the signal input/output end of the support plate and converge to form a second mutual, terminal electrode formation 19 in which terminal ends of the conductive tracks of the second group are shaped and arranged in a predetermined pattern and geometry dictated by the particular electro-chemical testing procedure they are intended to support for testing a blood sample of a selected/appropriate second sample volume. The signal input/output end of the support plate is an end which is opposite to the end of the rectangular support plate next to which the terminal electrode formations are positioned. The signal input/output end is designed to be removably inserted into sampling plate communications socket of a sample reader apparatus (e.g. handset) and presents terminal electrical contact ends of the conductive tracks arranged for electrically connecting with corresponding electrical signal contacts within the sample reader apparatus such that sample reader apparatus can apply predetermined electrical signals to selected conductive tracks of the support plate for application to a liquid blood sample held at the terminal electrode formations within the testing zones, according to an electro-chemical testing protocol, and can receive electrical signals from the blood samples in response, for analysis.

The first terminal electrode formation is different in geometry and structure to the geometry and structure of the second terminal electrode formation. Indeed, the two formations are formed from different numbers of convergent conductive signal tracks. The sample zone is arranged upon the support plate 15 and overlays the parts of the support plate leading to and immediately adjacent to the terminal electrode formations 18 and 19. The result is that the area of the support plate possessing the first terminal electrode formation 18 corresponds to the base area "A" exposed at the base of the first testing zone 6 of the laminate sample zone, and such that the second terminal electrode formation 19 corresponds to the base area "A" exposed at the base of the second testing zone 5 of the laminate sample zone. In this way the two testing zones which define different volumes according to the laminate structure of the sample zone, and possess different terminal electrode formations for supporting different electro-chemical tests appropriate to those respective volumes when filled with sample blood.

It is to be understood that the specifics of the geometry and structure of the terminal electrode formations may vary as desired or dictated by the requirements of whatever electrical signal structure/protocol is desired to be applied to and measured from the testing zone in question, and may differ from the example terminal electrode formations shown in the figures. Other terminal electrode formations would be readily apparent to the skilled person. By way of one, non-limiting example, for illustrative purposes, the terminal electrode formation 18 located in the first testing zone 6 may be arranged for measuring inter-cellular interferences. This type of measurement is better performed on relatively larger blood samples and so this is permitted by the relatively large volume of the first testing zone. Conversely, the second testing zone may be concurrently used to measure blood glucose levels within the sample, and a glucose oxidaze (GOx) may be provided (not shown) within the second testing zone for a measurement such as this, in which relatively less blood sample is required and, therefore, a smaller volume of the second testing zone ensures that the sample zone will be full with sufficient blood quickly.

The sample zone laminate comprises four substantially rectangular, flat and air-porous layers 2 each formed from a breathable hydrophobic material. Each of the four air-porous layers is separated from an immediately neighbouring air-porous layer by an intermediate, flat and solid (i.e. non-porous) spacer layer formed from a polymer film. Each of the three spacer layers and the four air-porous layers are substantially co-planar and share a generally rectangular outer profile such that the linear peripheral edges of any one of the layers is in register with those of the other layers.

Each one of three successive spacer layers 3 (e.g. a solid polymer film) is positioned between two neighbouring air-porous layers 2. The resulting laminate stack starts with a first air-porous layer 2A (FIG. 3) affixed to the planar upper surface of the support plate 15. Upon the first air-porous layer is arranged a first polymer spacer layer 3A, then a second air-porous layer 2B, then a second polymer spacer layer 3B, then a successive third air-porous layer 2C, then a subsequent third polymer spacer layer 3C and a final, uppermost fourth air-porous layer 2D. This laminar stack of seven successive layers is capped by a cover film 4 comprising a hydrophilic material.

The thickness of any one air-porous layer is substantially the same as that of any other of the air-porous layers 2. Similarly, the thickness of any one spacer layer 3 is substantially the same as that of any other of the spacer layers. However, in alternative embodiments the air-porous layers may be the same, but the spacer layers may vary in thickness from about 100 µm up to 1 mm, or perhaps more. This way one can control the liquid sample thickness using the spacer layers more than the air-porous layers. Indeed, in some embodiments air-porous layers may reside only at the top and bottom parts of the laminate stack and may sandwich between them a spacer layer which is thicker than any one of the air-porous layers, and may be as thick or thicker than the collective thickness of the air-porous layers. This means that air displaced by incoming liquid sample exits a testing zone via the top and bottom parts of the testing zone, and finally via the top part of the testing zone as that zone fills to the top. A benefit of using a majority of spacer material to define/control the height of a testing zone is that the porous nature of the air-porous layers may tend to capture air bubbles in the rough/"hairy" edges of the air-porous layers defining the walls of the testing zone. These bubbles may be an obstacle to liquid flow within the testing zone when filling and also reduce the overall volume available to be filled with liquid. Conversely, in not being air-porous and substantially smoother and less rough/"hairy" at its edges, a thick spacer layer is less susceptible to this bubble effect.

The first air-porous layer 2A attached to the surface of the support plate 15 possesses a re-entrant slot extending into the body of the layer from a peripheral linear edge of the layer. The re-entrant slot defines a first substantially linear slot portion 7 extending from the peripheral edge of the layer, a subsequent first circular slot portion 6 in fluid communication with the first linear slot portion, a second linear slot portion 8 extending from the first circular slot portion 6 in a direction generally transverse (e.g. substantially perpendicular) to the first linear slot portion 7 and a terminal second circular slot portion 5 which is in fluid communication with the first circular slot portion and the first linear slot portion via the second linear slot portion 8. The second linear slot portion 8 defines the fluid communication channel 8 linking the two testing zones. Each of the first and second circular slot portions is defined by a substantially circular slot edge or boundary formation surrounding an empty slot region of area A.

A first spacer layer 3A is attached to the upper surface of the first air-porous layer, in plane parallel orientation therewith, and possesses a re-entrant slot extending into the body of the layer from a peripheral linear edge of the layer. The re-entrant slot of the first spacer layer defines a substantially linear slot portion 7 extending from the peripheral edge of the layer, and a subsequent circular slot portion 6 in fluid communication with the linear slot portion. The re-entrant slot of the first spacer layer is substantially identical to, and arranged in register with, first linear slot portion 7 and the first circular slot portion 6 of the re-entrant slot of the first air-porous layer. This first spacer layer defines the ceiling of the second testing zone and presents a hydrophilic surface to the second testing zone 5. In particular the spacer body 3A comprises a hydrophilic material which may be a coating upon the spacer body, or may be substantially the material forming the spacer body. The hydrophilic surface is preferably be such as to produce a wetting angle of less than 30 degrees.

A second air-porous layer 2B is attached to the upper surface of the first spacer layer, in plane parallel orientation therewith, and possesses a re-entrant slot extending into the body of the layer from a peripheral linear edge of the layer. The re-entrant slot of the second air-porous layer has a shape and profile being substantially identical to that of the first spacer layer 3A. The re-entrant slot of the second air-porous layer is substantially identical to, and arranged in register with, linear slot portion 7 and the circular slot portion 6 of the re-entrant slot of the first spacer layer 2B.

A second spacer layer 3B is attached to the upper surface of the second air-porous layer, in plane parallel orientation therewith, and possesses a re-entrant slot extending into the body of the layer from a peripheral linear edge of the layer. A third air-porous layer 2C is attached to the upper surface of the second spacer layer 3B, in plane parallel orientation therewith, and also possesses a re-entrant slot extending into the body of the layer from a peripheral linear edge of the layer. A third spacer layer 3C is attached to the upper surface of the third air-porous layer, in plane parallel orientation therewith, and it too possesses a re-entrant slot extending into the body of the layer from a peripheral linear edge of the layer. A fourth air-porous layer 2D is attached to the upper surface of the third spacer layer 3C, in plane parallel orientation therewith, and once more, this layer also possesses a re-entrant slot extending into the body of the layer from a peripheral linear edge of the layer. The re-entrant slot of each one of the second and third spacer layers and each one of the third and fourth air-porous layers has a common shape and profile being substantially identical to that of the first spacer layer 3A. It is noted that the thickness of each spacer layer may be substantially the same but may differ from the thickness of each air-porous layer.

In alternative embodiments, the number of identical spacer layers may be reduced in the design shown in FIG. 3, such as by removing spacer layer 3C and/or 3B. Alternatively, one or more of those identical spacer layers may be replaced with identically-shaped additional air-porous layers. This would maintain the height "Z2" of the larger testing zone 6 while increasing the overall air-porosity of the circular walls of the testing zone. The thickness of a spacer layer could be from about 100 µm up to 1 mm, perhaps more. In the example shown in FIG. 1, the multiple layers of spacers and air-porous material could be reduced to three layers plus a cover film 4. For example, the first air-porous layer may define the footprint of both testing zones, a single, thicker spacer layer could be used, having a thickness of e.g. 0.5 mm. That thick spacer layer may then provide the ceiling for the second testing zone 5, and the extra height for the first testing zone 6. A second air-porous layer may complete the height of the second testing zone and provide the air escape route that allows it to fill to the ceiling. The cover film 4 would provide the ceiling for the deeper first testing zone.

In general, in embodiments where there are N testing zones within the sample zone, there may be N air-porous layers each defining at least a part of one of more of the N testing zones, and at least (N−1) spacer layers arranged individually between respective pairs of different successive air-porous layers. The different air-porous layers may be different in the sense that one such layer defines a different number (e.g. more) of testing zones, or a part thereof. For example, the lowest air-porous layer 2A of FIG. 3 defines not only a part of a first testing zone 6 and also defines the second testing zone 5. This is different to the neighbouring air-porous layer 2B which defines only a part of the first testing zone 6. In the example of FIG. 5, N=5. However, as shown in FIG. 3, N=2 and the laminar stack also comprises additional air-porous layers and spacer layers to increase the height "Z2" of the larger first testing zone 6 relative to the smaller second testing zone 5.

FIG. 5 illustrates (in isolation for clarity) a sample zone laminate structure 200 according to another embodiment of the invention. The sample zone laminate forms a part of the sampling plate (50, 200) shown in FIGS. 7, 8A and 8B. These figures are to be viewed in conjunction in the following description. The sampling plate comprises the sampling zone laminate structure affixed to a surface of a support plate 50 bearing electrodes which will be described in detail below. The support plate is omitted from FIGS. 5 and 6A to 6C for clarity only.

The sample zone comprises five discrete testing zones (21, 22, 23, 24 and 25), each for receiving different respective volumes of a fluid blood sample. Each testing zone presents a zone volume defined by the product of a respective zone base area ("A"; diameter e.g. 1.6 mm) of a size common to all testing zones, and a different respective zone height ("Z1"=200 microns, "Z2"=2×Z1; "Z3"=3×Z1; "Z4"=4×Z1; "Z5"=5×Z1; e.g. ranging from 200 microns in height to 1 mm in height amongst the five testing zones, in steps of 200 microns in height) being a dimension transverse to the zone area.

Figure 6A:
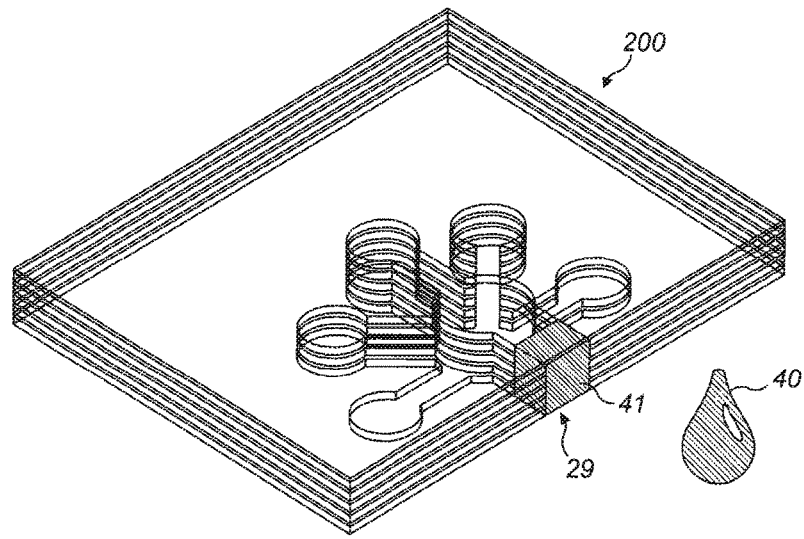
FIGS. 6A, 6B and 6C collectively illustrate successive stages in the loading of a liquid blood sample into the five discrete testing zones of the sample zone laminate structure of FIG. 5.
Figure 6B:
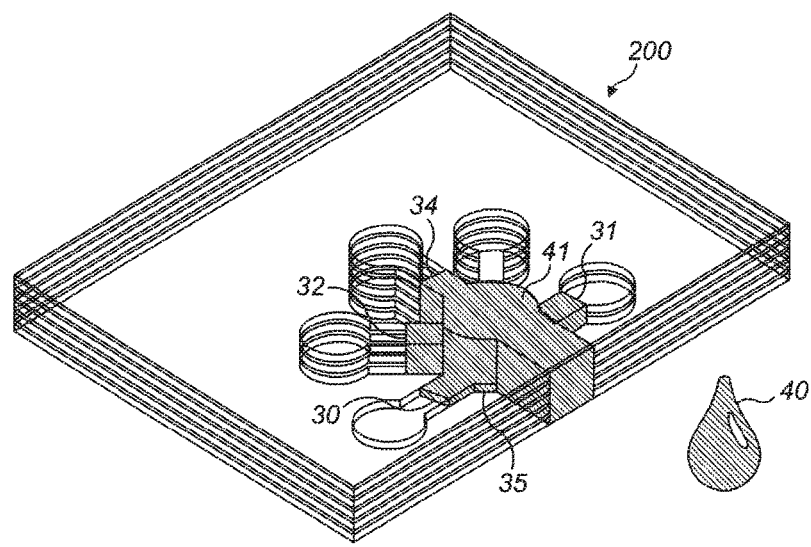
Figure 6C:
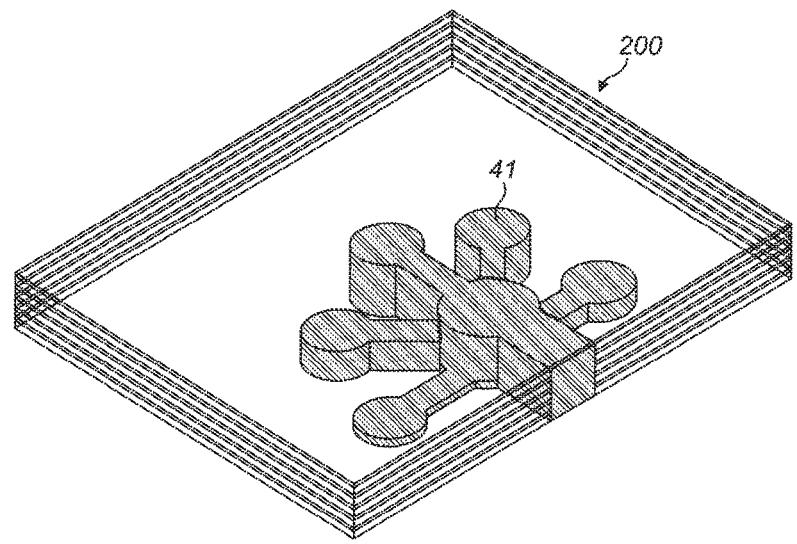

FIGS. 6A, 6B and 6C schematically illustrate the manner in which a volume 41 of a liquid blood sample 40 may enter and completely fill the two testing zones (21, 22, 23, 24 and 25) via a sample loading port 29 in fluid communication with each testing zone. To load and fill the testing zones, the fluid blood sample 40 is placed initially in fluid communication with the sample loading port 29 and is drawn into the loading port by capillary action. Further capillary action draws the fluid 41 into a central distribution chamber 35 in fluid communication with each one of the five testing zones and then into the those five testing zones via a respective one of five fluid communication channels (30, 31, 32, 33, 34) linking the central distribution chamber to a respective one of the five testing zones. Air displaced from the volume of the testing zones, the fluid distribution chamber, the five fluid communication channels and from the loading port 29, is received into air-porous laminar parts of the body of the sample zone by the advancing mass of liquid blood sample. Consequently, air bubbles which cause blockages to sample flow 41 into the testing zones, can be avoided or greatly minimised.

This process is completed when all five testing zones are filled with blood sample, as well as all fluid communication channels, the fluid distribution chamber and the loading port, as shown in FIG. 6C. Accordingly, each one of the five separate blood samples 41 are of different, known respective volumes (controlled by the geometry of the testing zones) in respective testing zones (21 to 25), ready for testing.

Figure 7:
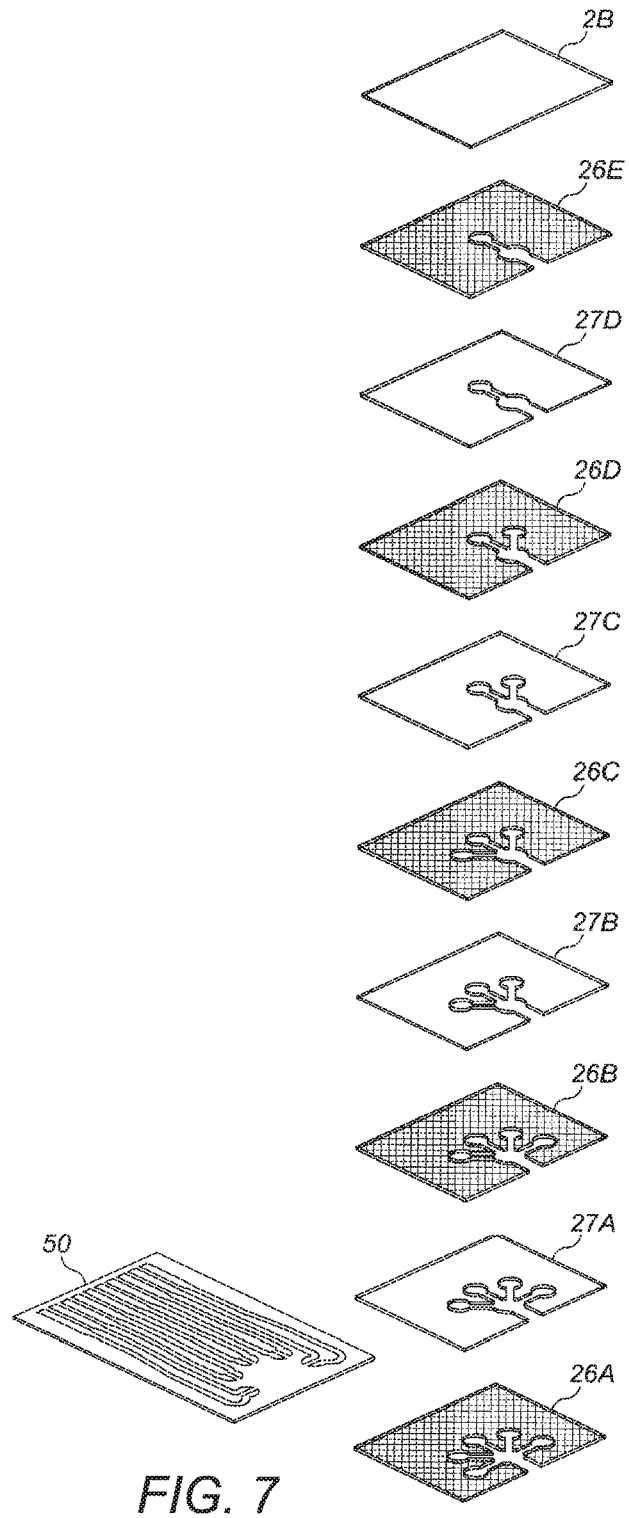
FIG. 7 illustrates an exploded view of the components of a sampling plate comprising the sample zone laminate structure of FIGS. 5 to 6C.
Figure 8A:
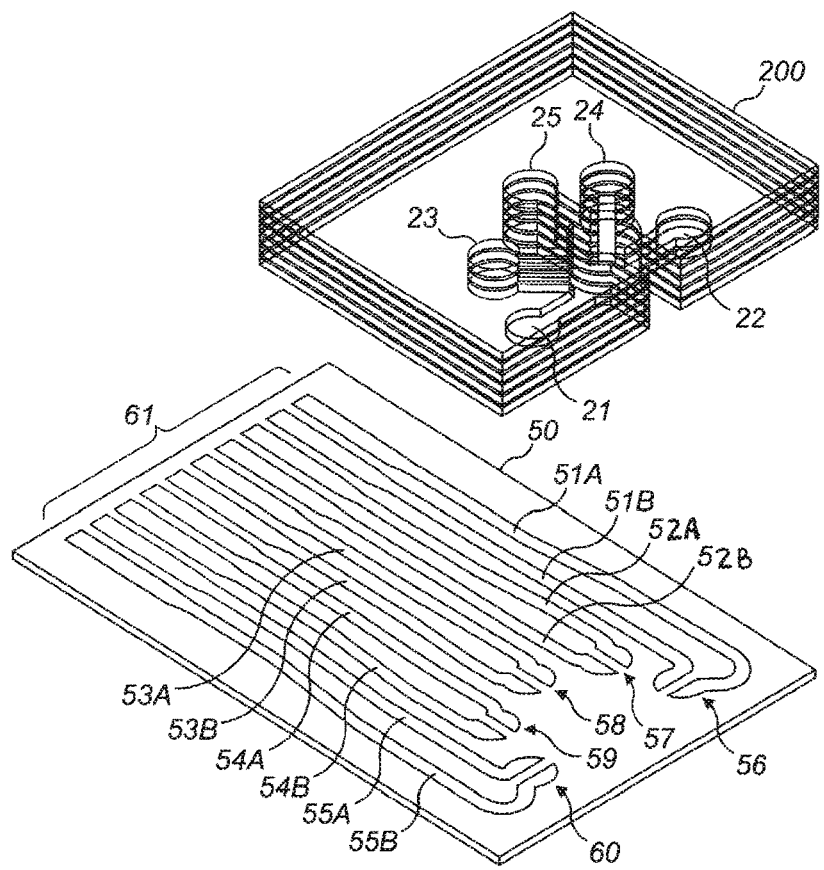
FIGS. 8A and 8B illustrate views of a sampling plate of FIG. 7. An exploded view is shown in FIG. 8A, and a view of the assembled sampling plate is shown in FIG. 8B.
Figure 8B:
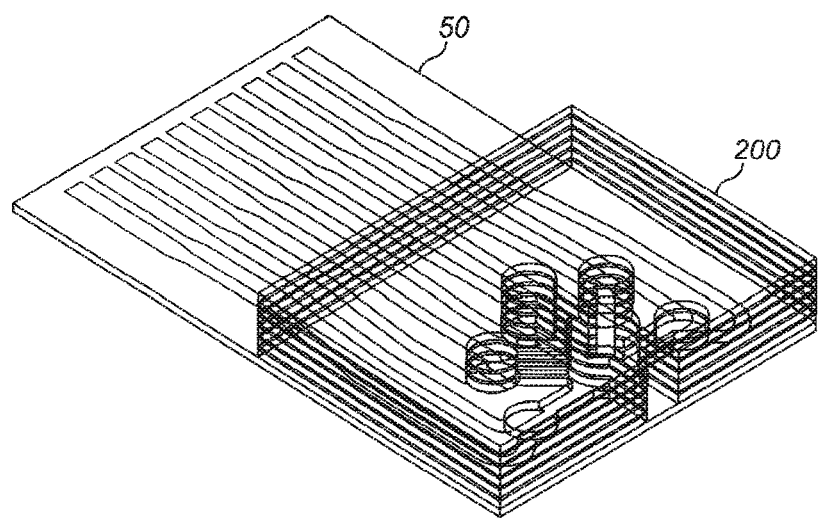

Referring to FIGS. 7, 8A and 8B, the support plate 50 comprises a plane rectangular base plate formed from a non-conductive and resiliently flexible material, such as a plastics material.

Upon one flat surface of the base plate are formed a ten of separate, conductive electrical signal conduction tracks (51A, 51B, 52A, 52B, 53A, 53B, 54A, 54B, 55A, 55B) defining five separate electrode pairs. Each pair is identified by a convergence of two neighbouring tracks at a terminal end to form a respective one or five terminal electrode formations (56, 57, 58, 59 and 60). The tracks may be thin printed layers of Gold or other suitable electrical signal conduction material.

Each conductive track extends in parallel with the other tracks from a signal input/output end of the support plate and converge in pairs to form the five terminal electrode formations in which terminal ends of the conductive tracks of each pair are shaped and arranged in a predetermined pattern and geometry dictated by the particular electro-chemical testing procedure they are intended to support for testing a blood sample of a selected/appropriate sample volume.

The signal input/output end of the support plate is an end which is opposite to the end of the rectangular support plate next to which the terminal electrode formations are positioned. The signal input/output end is designed to be removably inserted into sampling plate communications socket of a sample reader apparatus (e.g. handset) and presents terminal electrical contact ends of the conductive tracks arranged for electrically connecting with corresponding electrical signal contacts within the sample reader apparatus such that sample reader apparatus can apply predetermined electrical signals to selected conductive tracks of the support plate for application to a liquid blood sample held at the terminal electrode formations within the testing zones, according to an electro-chemical testing protocol, and can receive electrical signals from the blood samples in response, for analysis.

Each of the five terminal electrode formations is substantially the same in geometry and structure. The sample zone laminate structure 200 is arranged upon the support plate 50 and overlays the parts of the support plate that lead to and are immediately adjacent to the terminal electrode formations (56-60). The area of the support plate possessing any one of the five terminal electrode formations corresponds to a base area "A" exposed at the base of a respective one of the five testing zone (21-25) of the laminate sample zone. In this way the five testing zones which define different volumes according to the laminate structure of the sample zone, and possess a respective one of the five terminal electrode formations for supporting electro-chemical tests appropriate to those respective volumes when filled with sample blood.

It is to be understood that the specifics of the geometry and structure of the terminal electrode formations may vary as desired or dictated by the requirements of whatever electrical signal structure/protocol is desired to be applied to and measured from the testing zone in question, and may differ from the example terminal electrode formations shown in the figures. Other terminal electrode formations would be readily apparent to the skilled person. By way of one, non-limiting example, for illustrative purposes, the terminal electrode formations located in the five testing zones (56-60) may individually be arranged for measuring a respective one of: blood glucose levels, inter-cellular interferences, extra-cellular interferences, haematocrit levels (HCT), blood ketones. Each of these five different tests may desirably require, or benefit from, a relatively higher or lower blood sample volume within the testing zone and the variety of testing zone heights permits this on one sample strip. In this way, one sample strip may be able to perform a plurality of blood tests from one common sample, to enable the full metabolic state of the sample to be ascertained.

The electrode systems shown in FIGS. 7, 8A and 8B are for illustration purposes only. The form/design of the electrodes would be determined by the analytes being measured and the method used; i.e. AC or DC currents; or combined AC and DC; or electrochemical or photometric testing. The invention enables one to create different heights of liquid (e.g. blood) sample on the same test strip, thereby allowing different measurements to take place simultaneously.

The sample zone laminate 200 comprises five substantially rectangular, flat and air-porous layers (26A to 26E) each formed from a breathable hydrophobic material. Each of the five air-porous layers is separated from an immediately neighbouring air-porous layer by a respective one of four intermediate, flat and solid (i.e. non-porous) spacer layers (27A to 27D) formed from a polymer film. Each of the four spacer layers and the five air-porous layers are substantially co-planar and share a generally rectangular outer profile such that the linear peripheral edges of any one of the layers is in register with those of the other layers.

Each one of four successive spacer layers is positioned between two neighbouring air-porous layers. The resulting laminate stack starts with a first air-porous layer 26A (FIG. 7) affixed to the planar upper surface of the support plate 50. Upon the first air-porous layer is arranged a first polymer spacer layer 27A, then a second air-porous layer 26B, then a second polymer spacer layer 27B, then a successive third air-porous layer 26C, then a subsequent third polymer spacer layer 27C, then a successive fourth air-porous layer 26D, then a subsequent fourth polymer spacer layer 27D, and a final, uppermost fifth air-porous layer 26E. This laminar stack of nine successive layers is capped by a cover film 28 comprising a hydrophilic material.

The thickness of any one air-porous layer is substantially the same as that of any other of the air-porous layers. Similarly, the thickness of any one spacer layer is substantially the same as that of any other of the spacer layers. However, in alternative embodiments the air-porous layers may be the same, but the spacer layers may vary in thickness from about 100 µm up to 1 mm, or perhaps more. This way one can control the liquid sample thickness using the spacer layers more than the air-porous layers. Indeed, in some embodiments air-porous layers may reside only at the top and bottom parts of the laminate stack and may sandwich between them a spacer layer which is thicker than any one of the air-porous layers, and may be as thick or thicker than the collective thickness of the air-porous layers. This means that air displaced by incoming liquid sample exits a testing zone via the top and bottom parts of the testing zone, and finally via the top part of the testing zone as that zone fills to the top. A benefit of using a majority of spacer material to define/control the height of a testing zone is that the porous nature of the air-porous layers may tend to capture air bubbles in the rough/"hairy" edges of the air-porous layers defining the walls of the testing zone. These bubbles may be an obstacle to liquid flow within the testing zone when filling and also reduce the overall volume available to be filled with liquid. Conversely, in not being air-porous and substantially smoother and less rough/"hairy" at its edges, a thick spacer layer is less susceptible to this bubble effect.

The first air-porous layer 26A attached to the surface of the support plate 50 possesses a re-entrant slot extending into the body of the layer from a peripheral linear edge of the layer. The re-entrant slot defines a first substantially linear slot portion 29 extending from the peripheral edge of the layer, a subsequent first circular slot portion 35 in fluid communication with the first linear slot portion, five separate subsequent linear slot portions (30 to 34) extending from the periphery of the first circular slot portion 35 in a direction generally radial (e.g. each radiating in a direction from the centre) to the first circular slot portion 35 and a respective one of five corresponding terminal second circular slot portions (21 to 25) which are each in fluid communication with the first circular slot portion and the first linear slot portion via the respective subsequent linear slot portions (30 to 34). The subsequent linear slot portions (30 to 34) each define a fluid communication channel 8 linking the fluid distribution chamber 35 to the five testing zones. Each of the five terminal circular slot portions is defined by a substantially circular slot edge or boundary formation surrounding an empty slot region of area A.

A first spacer layer 27A is attached to the upper surface of the first air-porous layer, in plane parallel orientation therewith, and possesses a re-entrant slot extending into the body of the layer from a peripheral linear edge of the layer. The re-entrant slot defines a first substantially linear slot portion 29 extending from the peripheral edge of the layer, a subsequent first circular slot portion 35 in fluid communication with the first linear slot portion, and four separate subsequent linear slot portions (31 to 34) extending from the periphery of the first circular slot portion 35 in a direction generally radial to the first circular slot portion 35 and a respective one of four corresponding terminal second circular slot portions (22 to 25) which are each in fluid communication with the first circular slot portion and the first linear slot portion via the respective subsequent linear slot portions (31 to 34). The re-entrant slot of the first spacer layer is substantially identical to, and arranged in register with, corresponding parts of the re-entrant slot of the first air-porous layer.

A second air-porous layer 26B is attached to the upper surface of the first spacer layer, in plane parallel orientation therewith, and possesses a re-entrant slot extending into the body of the layer from a peripheral linear edge of the layer. The re-entrant slot of the second air-porous layer has a shape and profile being substantially identical to that of the first spacer layer 27A. The re-entrant slot of the second air-porous layer is arranged in register with the re-entrant slot of the first spacer layer 27A.

A second spacer layer 27B is attached to the upper surface of the second air-porous layer, in plane parallel orientation therewith, and possesses a re-entrant slot extending into the body of the layer from a peripheral linear edge of the layer. The re-entrant slot defines a first substantially linear slot portion 29 extending from the peripheral edge of the layer, a subsequent first circular slot portion 35 in fluid communication with the first linear slot portion, and three separate subsequent linear slot portions (32 to 34) extending from the periphery of the first circular slot portion 35 in a direction generally radial to the first circular slot portion 35 and a respective one of three corresponding terminal second circular slot portions (23 to 25) which are each in fluid communication with the first circular slot portion and the first linear slot portion via the respective subsequent linear slot portions (32 to 34). The re-entrant slot of the second spacer layer is substantially identical to, and arranged in register with, corresponding parts of the re-entrant slot of the second air-porous layer 26B.

A third air-porous layer 26C is attached to the upper surface of the second spacer layer, in plane parallel orientation therewith, and possesses a re-entrant slot extending into the body of the layer from a peripheral linear edge of the layer. The re-entrant slot of the third air-porous layer has a shape and profile being substantially identical to that of the second spacer layer 27B. The re-entrant slot of the third air-porous layer is arranged in register with the re-entrant slot of the second spacer layer 27B.

A third spacer layer 27C is attached to the upper surface of the third air-porous layer, in plane parallel orientation therewith, and possesses a re-entrant slot extending into the body of the layer from a peripheral linear edge of the layer. The re-entrant slot defines a first substantially linear slot portion 29 extending from the peripheral edge of the layer, a subsequent first circular slot portion 35 in fluid communication with the first linear slot portion, and two separate subsequent linear slot portions (33 to 34) extending from the periphery of the first circular slot portion 35 in a direction generally radial to the first circular slot portion 35 and a respective one of two corresponding terminal second circular slot portions (24 to 25) which are each in fluid communication with the first circular slot portion and the first linear slot portion via the respective subsequent linear slot portions (33 to 34). The re-entrant slot of the third spacer layer is substantially identical to, and arranged in register with, corresponding parts of the re-entrant slot of the third air-porous layer 26C.

A fourth air-porous layer 26D is attached to the upper surface of the third spacer layer, in plane parallel orientation therewith, and possesses a re-entrant slot extending into the body of the layer from a peripheral linear edge of the layer. The re-entrant slot of the fourth air-porous layer has a shape and profile being substantially identical to that of the third spacer layer 27C. The re-entrant slot of the fourth air-porous layer is arranged in register with the re-entrant slot of the third spacer layer 27C.

A Fourth spacer layer 27D is attached to the upper surface of the fourth air-porous layer, in plane parallel orientation therewith, and possesses a re-entrant slot extending into the body of the layer from a peripheral linear edge of the layer. The re-entrant slot defines a first substantially linear slot portion 29 extending from the peripheral edge of the layer, a subsequent first circular slot portion 35 in fluid communication with the first linear slot portion, and one separate subsequent linear slot portion 34 extending from the periphery of the first circular slot portion 35 in a direction generally radial to the first circular slot portion 35 and a respective corresponding terminal second circular slot portion 25 which is in fluid communication with the first circular slot portion and the first linear slot portion via the subsequent linear slot portion 34. The re-entrant slot of the fourth spacer layer is substantially identical to, and arranged in register with, corresponding parts of the re-entrant slot of the fourth air-porous layer 26D.

A fifth air-porous layer 26E is attached to the upper surface of the fourth spacer layer, in plane parallel orientation therewith, and possesses a re-entrant slot extending into the body of the layer from a peripheral linear edge of the layer. The re-entrant slot of the fifth air-porous layer has a shape and profile being substantially identical to that of the fourth spacer layer 27D. The re-entrant slot of the fifth air-porous layer 26E is arranged in register with the re-entrant slot of the fourth spacer layer 27D.

One, some or each spacer layer (27A-27D), and/or the ceiling layer 28, may present a hydrophilic surface to a respective testing zone of which it forms a part. In particular a surface of one or each of the spacer layers which defines a floor or ceiling of a testing zone may be hydrophilic. A spacer layer may comprise a hydrophilic material which may be a coating upon the spacer body, or may be substantially the material forming the spacer body. Similarly, the upper surface of the support plate 50 may present a hydrophilic coating in the region thereof which is in register with the loading port 29, the distribution chamber 35 and each of the slot portions (30-34). The hydrophilic surface may preferably be such as to produce a wetting angle of less than 30 degrees.

The detection and/or measurement technology for sample plates may be designed may be electronically based (e.g. electrochemistry and/or impedance methods) or optically based (e.g. photometric, light absorbance and/or light reflection). In preferred embodiments of the invention the testing strip may carry electrochemistry sensors or photometric (absorbance or reflectance) sensors or both. The invention provides a means of creating different liquid (e.g. blood) sample sizes (in the X-Y plane and in the Z direction) at various positions on the same test strip. How those samples are interrogated (electrochemically or photometrically) is a matter of choice. For example, a diabetes test strip may be provided with multi tests (one per testing zone) including BG, ketones, HbA1c and haematocrit. How each of these analytes is detected and measured may be a matter of choice. For example, a combined electrochemical and photometric platform may be provided if desirable for performance for the tests. The test strip may be a photometric strip and may comprise transparent layers at the floor (15, 50) and ceiling (4, 28) of one, some or each of the testing zone(s). Thereby the design of the support plate and cover plates of the sample strip herein may include materials that allow light paths to pass through them and through samples within testing zones.

The thickness of each breathable material layer is preferably the same and in the range of 80 µm to 500 µm. The breathable material may have a hydrophobic nature or surface treatment to prevent the fluidic sample flowing into the material as the air escapes from the sample plate. The thickness of the spacer layers (e.g. solid polymer films) may vary within the sample plate design; i.e. each spacer thickness may be specific to the requirements of the sensor that its pathway supplies. The thickness of a spacer layer may be in the range of 20 µm to 1 mm.

The embodiments illustrated exemplify how the sensor system employed with the invention to detect and/or measure analytes may be electronically based, and more specifically electrochemistry based. The floor of testing zones carries a series of conductive electrodes arranged to be used to apply AC and/or DC voltages and/or currents to the fluidic sample and detect and/or measure a response. Such responses would be indicative of the presence and/or concentration of a particular analyte in the fluidic sample.

Example

A sampling plate may be used to measure blood glucose in whole blood. It would carry a dried deposit of biochemical solution, such as glucose oxidase, and would be powered by a DC voltage (of the order of 400 mV). The blood applied to the sensor causes an electrochemical reaction to take place, the output of which is a transient response curve. The sensor would be connected to an electronic system that would collect, analyse and interpret the transient response curve in order to present a measurement result. Embodiments that utilise optical based detection and/or measurement techniques may have light pathways running in the Z direction through the sensor areas. When the fluidic sample is present the light pathway could be used to detect and/or measure the presence and/or concentration of a particular analyte.

Example

A sampling plate may comprise of an optical pathway into which the fluidic sample would flow. Within a testing zone could lie a dried chemistry deposit that reacts with an analyte in the fluidic sample. The reaction would cause a change in the optical density of the fluidic sample which would be measured as a change in the amount of light transmitted through the fluidic sample. The change in optical density could be used as a YES/NO answer to the presence of the analyte, or the rate of change of optical density could used to measure the concentration of the analyte.

Further embodiments could include combinations of electronic based and optical based sensor systems.

It is to be understood that the embodiments described herein are for illustrative purposes and modifications, variants and equivalents to details thereof such as would be apparent to the skilled reader are encompassed within the scope of the invention such as is defined by the claims.

The invention claimed is:

1. A sampling plate for use in measuring a property of a fluid sample comprising:
   a sample zone comprising at least two discrete testing zones for receiving different respective volumes of the fluid sample;
   wherein each said testing zone presents a zone volume defined by a respective zone area and a different respective zone height being a dimension transverse to the zone area;
   the sampling plate comprises a support plate bearing a laminate structure of layers including a plurality of separate non-porous layers and a plurality of separate air-porous layers spaced from one another in said dimension transverse to the zone areas by a respective intermediate said non-porous layer which thereby provides a spacer layer wherein successive said layers of the laminate structure each comprise an empty portion formed therein for containment of the fluid sample and arranged mutually in register collectively to define a said zone height of a testing zone, whereby an air-porous layer of a testing zone receives air displaced from a respective testing zone as the fluid sample is received into the testing zone; and,
   wherein a spacer layer provides:
   (a) a said zone area of one or more of said testing zones of the sample zone; and,
   (b) a said empty portion within one or more other said testing zones of the sample zone.

2. A sampling plate according to claim 1 in which the size of a said respective zone area is common to some or all of said testing zones.

3. A sampling plate according claim 1 including a sample loading port in fluid communication with said plurality of testing zones.

4. A sampling plate according to claim 1 in which some or all of said zone areas are substantially coplanar.

5. A sampling plate according to claim 1 in which a said zone volume is substantially defined by the product of the respective said zone area and zone height.

6. A sampling plate as claimed in claim 1 wherein the air porous body is located substantially around the perimeter of a respective testing zone.

7. A sampling plate according to claim 1 in which said plurality of air-porous bodies share a substantially common thickness in said transverse dimension.

8. A sampling plate according claim 1 comprising a plurality of spacer bodies which share a substantially common thickness in said transverse dimension.

9. A sampling plate according to claim 1 wherein the air porous body is substantially impermeable to water.

10. A sampling plate as claimed in claim 1 wherein the air porous body is arranged to hold the liquid sample within the sample zone.

11. A sampling plate as claimed in claim 1 wherein the air porous body comprises hydrophobic material.

12. A sampling plate according to claim 1 in which each testing zone is accessible via a zone access port having same height as the height of the associated zone.

13. A sampling plate as claimed in claim 1 wherein the sample zone comprises at least one hydrophilic floor for containing the liquid sample.

14. A sampling plate according to claim 1 comprising transparent layers defining the floor and ceiling of one, some or each of the testing zone(s) to allow light paths to pass through them.

15. A sampling plate according to claim 1 comprising conductive electrodes formed on the floor or ceiling of one, some or each of the testing zone(s) to allow electrical signals to pass between them when, in use, bridged by a liquid sample therein.

16. A method of manufacturing a sampling plate for use in measuring a property of a fluid sample and including a sample zone comprising at least two discrete testing zones which have different respective volumes for containment of corresponding volumes of the fluid sample wherein each said testing zone presents a zone volume defined by a respective zone area and a different respective zone height, the method, comprising:
   providing a plurality of separate air-porous layers each comprising an empty portion arranged to receive and contain the fluid sample;
   providing a plurality of separate non-porous layers each comprising an empty portion arranged to receive and contain the liquid sample;
   providing a support plate;
   forming a laminate structure of layers on the support plate comprising a plurality of said air-porous layers each mutually spaced from one another by a respective intermediate said non-porous layer which thereby provides a spacer, thereby to form said laminate structure defining a sampling plate layer in which respective said empty portions of successive said layers of the laminate structure are arranged mutually in register to define said zone height of a testing zone in a dimension transverse to the zone area; and
   wherein the forming of the laminate structure includes arranging a spacer layer therein to provides:
   (a) a said zone area of one or more of said testing zones of the sample zone; and,
   (b) a said empty portion within one or more other said testing zones of the sample zone; such that said sample zone is formed comprising at least two discrete testing zones which have different respective volumes for containment of corresponding volumes of the fluid sample, said zone volume defined by a respective said zone area and a different respective said zone height.

* * * * *